United States Patent
Ruha

(10) Patent No.: US 6,282,439 B1
(45) Date of Patent: Aug. 28, 2001

(54) METHOD OF MEASURING VITAL FUNCTION AND MEASURING DEVICE

(75) Inventor: Antti Ruha, Oulu (FI)

(73) Assignee: Polar Electro Oy, Kempele (FI)

( * ) Notice: Subject to any disclaimer, the term of this patent is extended or adjusted under 35 U.S.C. 154(b) by 0 days.

(21) Appl. No.: 09/412,485

(22) Filed: Oct. 5, 1999

(30) Foreign Application Priority Data

Oct. 8, 1998 (FI) .................................................. 982192

(51) Int. Cl.$^7$ ........................................................ A61B 5/04
(52) U.S. Cl. ........................ 600/509; 600/516; 600/300
(58) Field of Search .................................. 600/509, 516, 600/517, 521, 508, 500, 300

(56) References Cited

U.S. PATENT DOCUMENTS

| | | | |
|---|---|---|---|
| 3,759,248 | * 9/1973 | Valiquette et al. | 600/516 |
| 4,721,114 | * 1/1988 | DuFault et al. | 600/509 |
| 5,323,783 | * 6/1994 | Henkin et al. | 600/516 |
| 5,687,735 | 11/1997 | Forbes et al. . | |
| 5,690,118 | * 11/1997 | Sornmo et al. | 600/509 |
| 5,840,038 | * 11/1998 | Xue et al. | 600/512 |

FOREIGN PATENT DOCUMENTS

| | | |
|---|---|---|
| 310349 | 4/1989 | (EP) . |
| 100452 | 12/1997 | (FI) . |

OTHER PUBLICATIONS

Rhyhe, V. Thomas, "A Comparison of Coherent Averaging Techniques for Repetitive Biological Signals", Medicl Research Engineering, Aug.–Sep., 1969, vol. 8, pp. 22–26.*

* cited by examiner

Primary Examiner—John P. Lacyk
Assistant Examiner—Navin Natnithithadha
(74) Attorney, Agent, or Firm—Hoffman & Baron, LLP

(57) ABSTRACT

The invention relates to a method of measuring a vital function and a measuring device implementing the method. The measuring device receives for example heart pulses as signal episodes. The measuring device calculates a coherent average of the signal episodes in an averaging unit to determine the wave form of the signal episode. The measuring device also preferably comprises an adapted filter the impulse response of which is based on the coherent average of the signal episode.

35 Claims, 6 Drawing Sheets

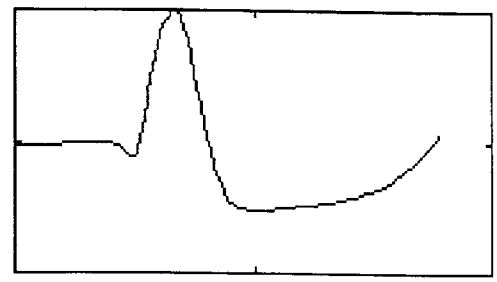
FIG. 1B  FIG. 1C
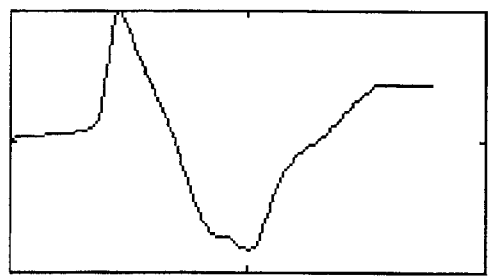
FIG. 1D  FIG. 1E
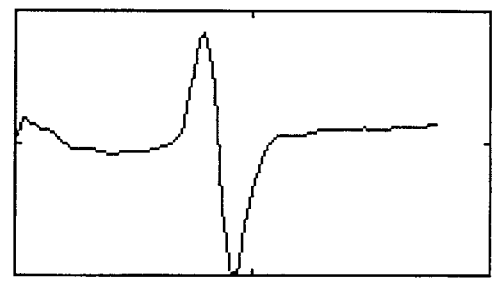
FIG. 1F

METHOD OF MEASURING VITAL FUNCTION AND MEASURING DEVICE

FIELD OF THE INVENTION

The invention relates to measuring a vital function, and particularly to measuring the heart rate.

BACKGROUND OF THE INVENTION

Prior art solutions utilize filtering and a detection threshold for detecting the heart rate. In filtering the frequency band of the received signal is limited so that preferably only the heart rate signal passes through the filter. Furthermore, when the heart rate is calculated, only pulses which have a sufficiently high amplitude and exceed (or are below) the detection threshold are taken into account.

The disadvantages of the prior art solutions include the fact that they do not take the different forms of the QRS complex the heart rate into account, even though different persons may have very different QRS complex widths and wave forms. This can also easily lead to incorrect heart rate detection especially if there is interference in the environment. By adapting the detection method and measuring device to each person's own QRS signal, heart rate detection and wave form recognition can be improved and made more reliable.

BRIEF DESCRIPTION OF THE INVENTION

The object of the invention is to provide a method and a measuring device implementing the method to solve the above-mentioned problems. The invention relates to a method of measuring a recurrent signal episode of a vital function, the method employing an adapted filter for detecting the signal episode. The method of the invention comprises calculating a coherent average of single signal episodes to determine the wave form of the signal episode. The invention also relates to a method of determining the impulse response of a recurrent signal episode of a vital function in a detector based on an adapted filter. The method of the invention comprises calculating a coherent average of single signal episodes and employing the coherent average of the signal episode for forming the impulse response of the adapted filter.

The invention also relates to a measuring device for measuring a recurrent signal episode of a vital function, the measuring device comprising electrodes for receiving signal episodes generated by the vital function and an adapted filter for detecting the signal episodes received by the electrodes. The measuring device of the invention comprises a coherent averaging unit which is arranged to determine the wave form of the signal episode received by the electrodes. The invention also relates to a measuring device for measuring a recurrent signal episode of a vital function, the measuring device comprising electrodes for receiving the signal episodes generated by the vital function. The measuring device according to the invention comprises a coherent averaging unit which is arranged to calculate the coherent average of the signal episodes received by the electrodes, and an adapted filter the impulse response of which is based on the coherent average of the signal episode.

The method and measuring device of the invention offer several advantages. The measuring device is capable of adapting to changing wave forms. One important feature of the solution is that it combines good noise tolerance with quick learning and adaptation to changing wave forms. This is a significant feature in the measurement of the heart rate and the exercise-electrocardiogram (EKG), for example, where the form of the QRS complex may change due to exertion or displacement of the electrodes.

BRIEF DESCRIPTION OF THE DRAWINGS

The invention will be described in greater detail by means of preferred embodiments with reference to the accompanying drawings, in which FIGS. 1B to 1F illustrate different QRS complexes.

DETAILED DESCRIPTION OF THE INVENTION

The solution of the invention can be applied in medical measurements, particularly in heart rate measurements and in the analysis of the EKG signal form.

Figure 1A:
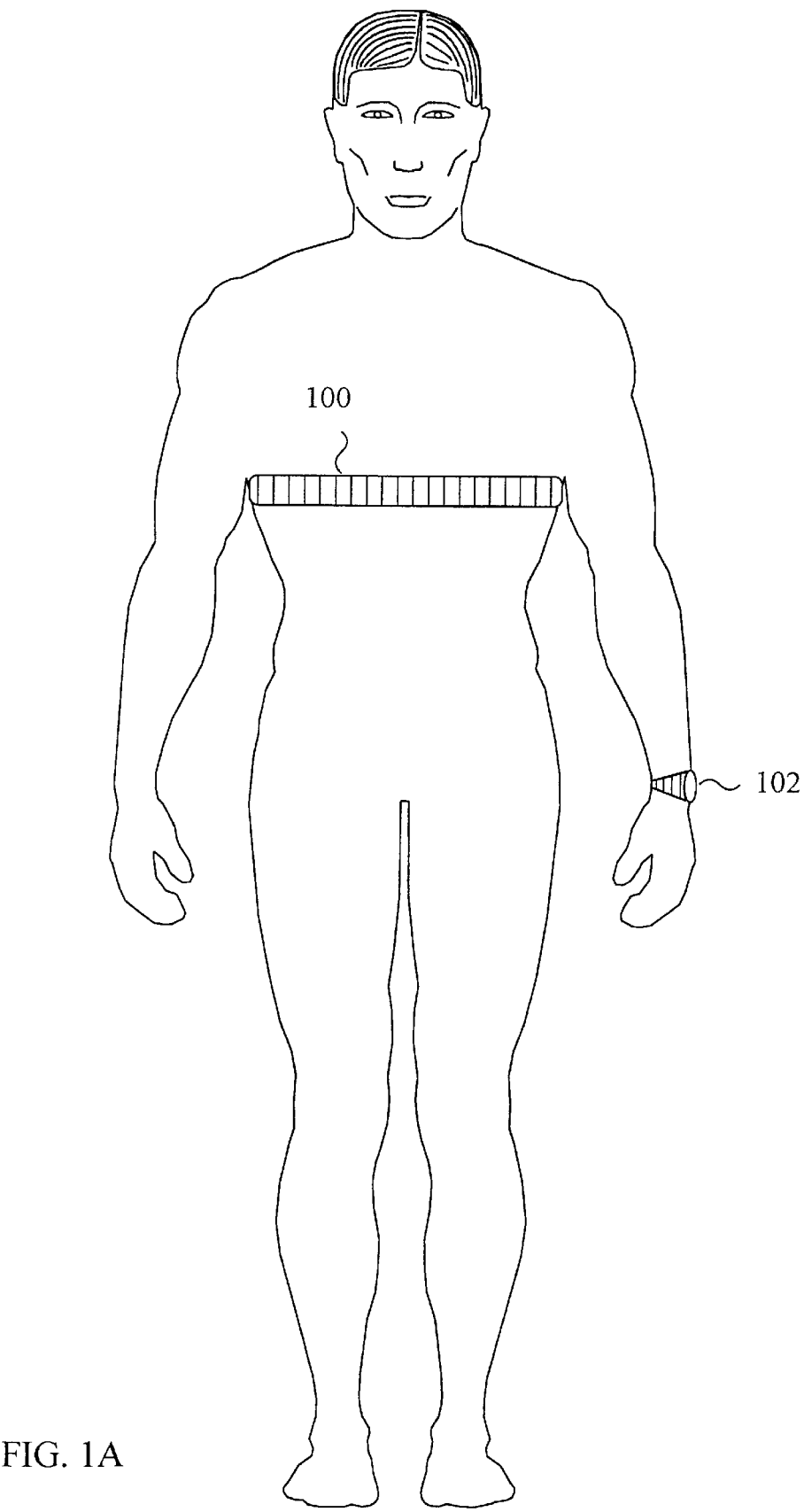
FIG. 1A illustrates a user wearing a measuring device.

FIG. 1A illustrates a preferred embodiment of the present invention, i.e. a heart rate meter. The heart rate meter comprises a transmitter unit 100 which is attached around the user's chest and measures the heart rate. The user also wears the receiver unit 102 of the system on his wrist, for example.

FIGS. 1B to 1F illustrate different measured QRS complexes. All QRS complexes are illustrated in the same system of coordinates where the vertical axis represents the amplitude of the signal episode used as the QRS complex on a freely-chosen scale and the horizontal axis represents the time in seconds. The pulse form is affected by personal differences (differences between individual animals and animal species when animals are measured), attachment and location of the electrodes and different interfering factors, such as discharge of static electricity between the shirt and the skin.

Figure 2:
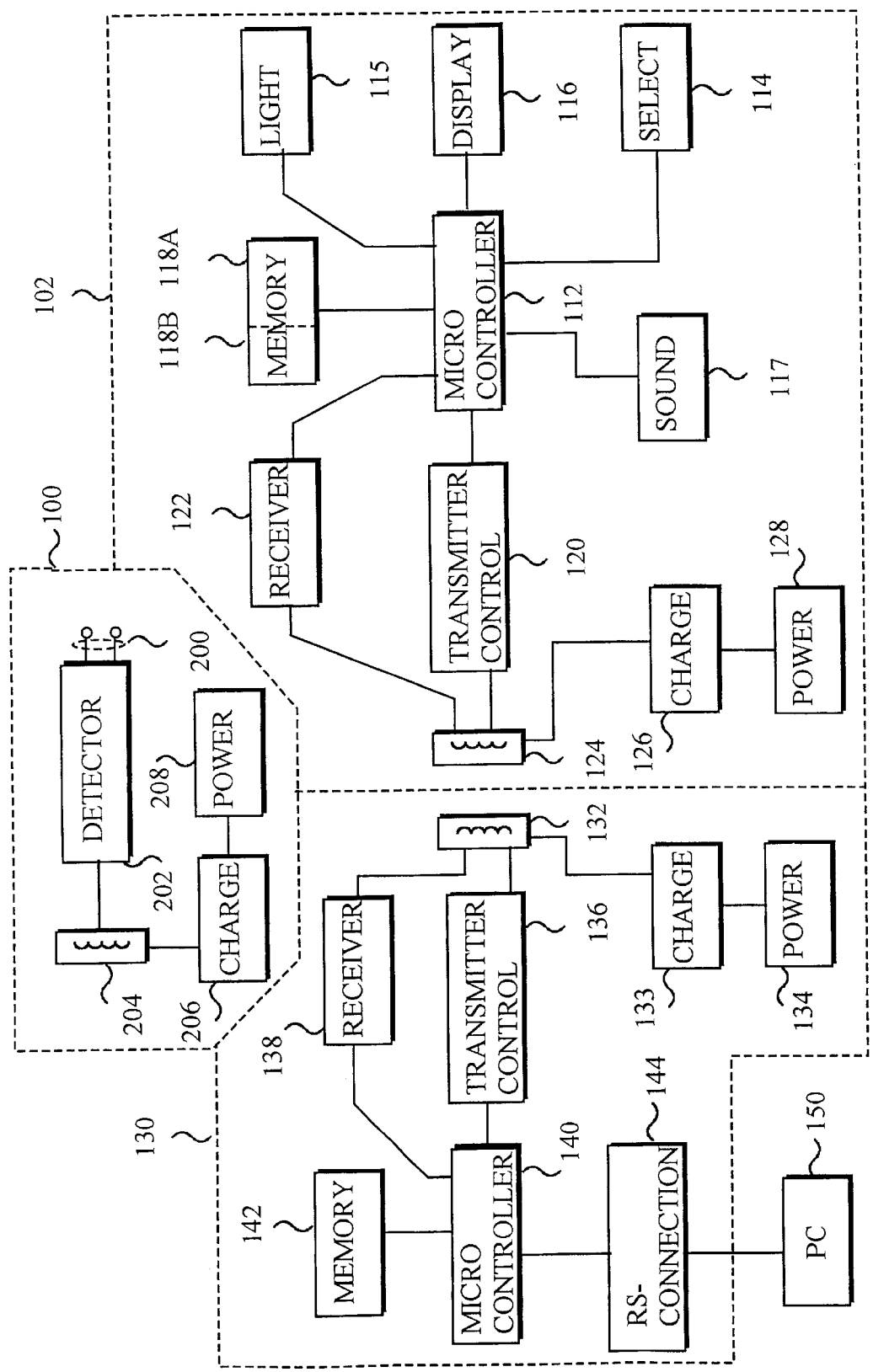
FIG. 2 illustrates a measuring arrangement for the heart rate.

First we shall examine an arrangement for measuring the heart rate as an example of a device measuring a vital function. FIG. 2 illustrates a device measuring the heart rate. The main components of the system are a telemetric transmitter unit 100, telemetric receiver unit 102, data transmission unit 130 and data processing and controlling unit 150, which may be e.g. a PC. In the embodiment of FIG. 2 a transmission unit 100 known per se can be used, the unit comprising EKG electrodes 200, a block 202 for pre-amplifying the EKG and detecting the pulse, inductance 204, charging block 206 and power source 208. The output received from the block 202 is a heart rate signal which corresponds to the heart rate and controls the inductance, i.e. induction coil 204. Thus a magnetic field alternating at the heart rate is generated to the inductance 204, which inductively interacts with the induction coil 124 of the receiver through the magnetic field. The power source 208 produces the electric power needed by each block of the transmitter unit 100 (for the sake of clarity the power supply wires are not illustrated in FIG. 2). If desired, the power source 208 can be charged by transferring electric energy via the induction coil 204. The charging block 206 is responsible for disturbance-free charging.

The transmitter unit 100 may also comprise a memory, in which case the transmitter unit 100 does not need to be paired with a receiver unit 102, but the transmitter unit 100 stores the measurement data in its memory from which the measurement data are unloaded to a computer 150 via the data transmission unit 130 for processing and analysis, for example.

The receiver unit 102 comprises a control part 112. The control part 112 also controls a user interface which comprises selection means 114 and display means 116. The selection means 114 is typically a keyboard by means of which the user employs the receiver unit 102. The display means 116, such as an LCD display, conveys visual information to the user. The receiver unit typically also comprises a light source 115 for illuminating the display 116, particularly when it is dark, and a sound signalling device 117. The control part 112 is typically a microprocessor which comprises a ROM memory 118A in which the software controlling the device is stored. The device may also contain additional memory 118B in which the data gathered during the measuring can be stored, e.g. information on the heart rate, time and other user-specific parameters. The control part 112 may also be implemented using an ASIC circuit or other electronic components. The receiver 102 further comprises a transmission controller 120, receiver means 122 and inductance 124. The transmission controller 120 generates data transmission from the receiver unit 102 to the data transmission unit 130 using the inductance 124. By means of the inductance 124 the receiver means 122 receive information in the form of induced voltage from the inductance 132 of the data transmission unit 130 and converts it to a digital form for the microprocessor 112. The receiver means 122 are included in the pulse detection block 202 or the like and preferably comprise an adapted filter of the invention. The inductance 124, such as a coil, is excited to resonance by means of a capacitor (not shown) using the frequency employed for data transmission. The receiver unit 102 also comprises a power source 128, which may be e.g. a battery, accumulator, rechargeable battery or the like. The charging part 126 is responsible for charging the rechargeable battery. The power source 128 feeds electric power into each block of the receiver unit 102 (for the sake of clarity the power supply wires are not illustrated in FIG. 2). The power source 128 can also be charged by transferring electric energy via the induction coil 124. The charging block 126 is responsible for disturbance-free charging.

The receiver unit 102, which is typically worn on the wrist like a watch, may also independently measure the users heart rate or another vital function by means of sensors 119. The measuring can be performed optically and/or with a pressure sensor according to the prior art. In that case the receiver unit 102 substantially functions both as the receiver 102 and as the transmitter 100, i.e. a separate transmitter unit 100 is not a necessary part of the measuring system.

The data transmission unit 130 comprises an inductance 132, transmission controller 136, receiver means 138, computing unit such as a microprocessor 140, memory 142 and interface 144. The data transmission unit 130 communicates with the data processing unit 150, such as a PC, via the interface 144. The inductance 132 of the data transmission unit 130 is at the same resonance frequency as the inductance 124 of the receiver unit. The purpose of the transmission controller 136 is to generate a control signal for the inductance 132. The purpose of the receiver means 138 is to receive incoming serial data from the inductance 124 via the inductance 132. The microprocessor 140 converts the transmitted data to a suitable form for the PC (data processing unit 150). The memory 142 of the data transmission unit 130 may store files that have been read, if necessary. The interface 144, such as RS232, converts the voltage levels of the interface to suit the interface that is used. The power source 128 feeds electric power into each block of the data transmission unit 130 (for the sake of clarity the power supply wires are not illustrated in FIG. 2). In the inventive solution the power source 134 can be charged by transferring electric energy via the induction coil 132. The charging block 133 is responsible for disturbance-free charging.

Now we shall describe the method of the invention. The method of the invention allows to obtain an accurate signal estimate of a vital function even when measurements contain interference. The signal estimate is calculated using coherent averaging. An advantageous feature of the solution is that the quality (SNR or the like) of each signal episode used for coherent averaging is estimated. By using a high SNR or other weighting functions which the ratio between the signal and the noise, it is possible to obtain a noise immune system, i.e. a system which is insensitive to the influence of signals deviating from the signal estimate. One way of estimating the signal-to-noise ratio is to measure the similarity of successive signal episodes. Another alternative is to compare the similarity of the wave forms of the signal episode and the signal estimate obtained by averaging. In averaging signal episodes with a good signal-to-noise ratio are given more weight than signal episodes with a poor signal-to-noise ratio. Signal estimates can be used for two purposes. The signal estimate can be employed for determining the impulse response of the adapted filter or for analyzing the wave form of the signal.

Figure 3:
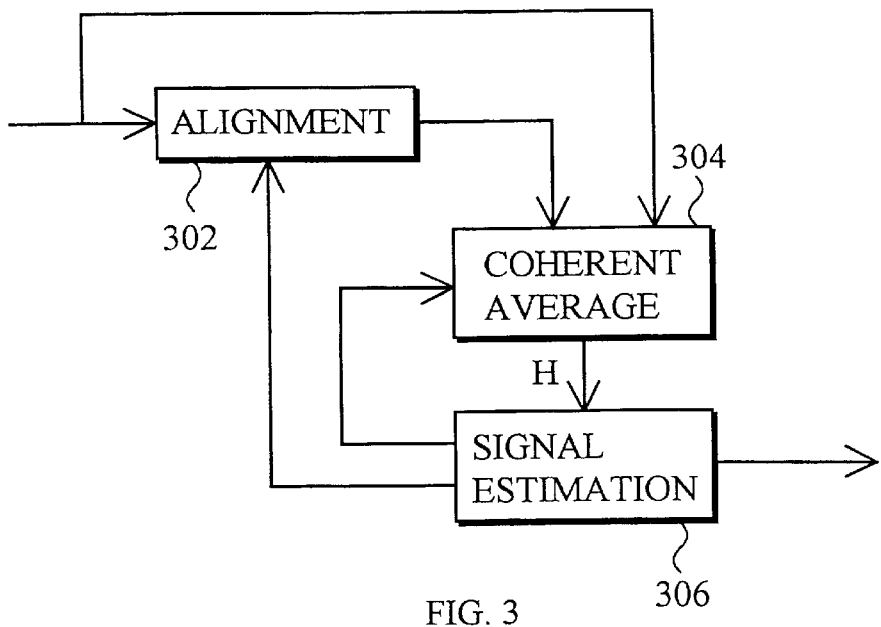
FIG. 3 illustrates a measuring arrangement employing coherent averaging.

In the following, the method and measuring device of the invention will be described in greater detail with reference to FIGS. 3 to 5. FIG. 3 illustrates signal estimation by means of coherent averaging. The arrangement comprises an adjustment block 302, coherent averaging block 304 and signal estimation block 306. A data signal $QRS_s$ received from the unit measuring the QRS complex is supplied to the signal estimation block 306. These blocks of the invention may be located in the transmitter unit 100 (e.g. in block 202) or in the receiver unit 102 (e.g. in block 122) of the heart rate meter illustrated in FIG. 2. When measuring is initiated, the characteristic wave form of the heart rate, which is simply a triangle or a typical measured EKG curve, is used as the signal estimate in block 306, for instance. The reference signal, which may be an earlier signal episode or the average of earlier signal episodes, and the received data signal $QRS_s$, i.e. the new signal episode, are adjusted in block 302 so that the adjustment between the reference signal and the new signal episode is optimal. This is performed by means of correlation, for example. The correlation C is calculated digitally as a cross product for sequences X (e.g. the reference signal) and Y (e.g. the new signal episode) in the following manner, for example:

$$C(n) = \sum_{i=1}^{N} x(i)y(n+i)$$

where each C(n) corresponds to the elementary unit of correlation C, and n and i are computational indices. When the signal and the estimate match, coherent averaging is performed on the signal $QRS_s$ and the estimate in block 304. An impulse response H, which typically corresponds to the wave form of the signal, is determined by means of coherent averaging. The impulse response can be used e.g. for determining the transmission function of the adapted filter in solutions in which heart rate detection is based on the adapted filter.

Figure 4:
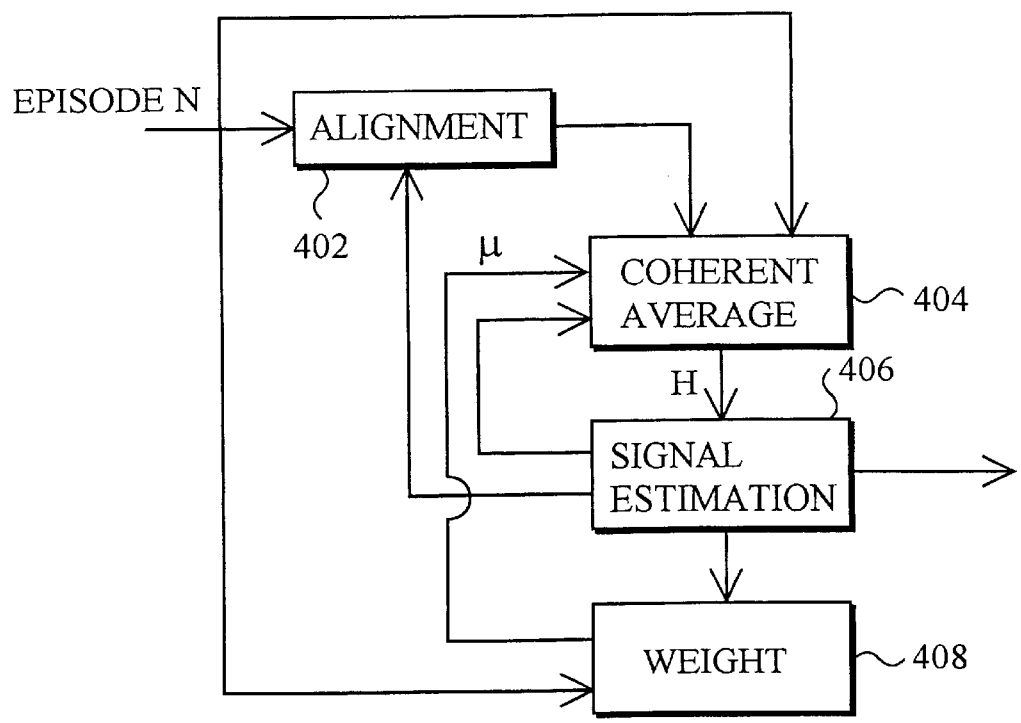
FIG. 4 illustrates a measuring arrangement employing coherent averaging and weighting.

A more accurate result is, however, achieved with the solution of FIG. 4 where the signal estimate average to be calculated is weighted for calculation of the average. The solution comprises a signal estimate and a signal adjustment block 402, coherent average calculation block 404, signal estimate determination block 406 and weighting block 408. In this solution the new signal episode is added to the signal estimate after it has been weighted with a weighting value $\mu(SNR)$ which depends on the quality of the signal episode. Thus the new impulse response $H_{new}$ is obtained as follows: $H_{new}=H_{old}\cdot(1-\mu(SNR)\cdot det_{uth})+\mu(SNR)\cdot det_{uth}\cdot QRS_s$ where $H_{old}$ is the impulse response of the preceding iteration cycle and $det_{uth}$ represents adjustment of the signal and the signal estimate (when these match, $det_{uth}=1$). In the solution of the invention the magnitude of the weighting value $\mu(SNR)$ is determined by the quality of the received signal episode $QRS_s$. The signal quality is measured in the weighting unit 408 preferably with the signal-to-noise ratio SNR by comparing the received signal episode $QRS_s$ with the averaged signal episode estimate. The difference between the signal episodes to be compared results mainly from the noise the signal contains. Instead of or in addition to the signal-to-noise ratio, other values which indicate the signal quality and are obvious to a person skilled in the art, such as the signal-interference ratio, can be employed, too. Similarity can be compared in numerical form by means of software or DSP hardware using the ML estimate (maximum likelihood), sample correlation coefficient or energy transmission. The sample correlation factor and energy transmission, which are determined in a manner known to a person skilled in the art, are normalized variables independent of the amplitude, and consequently they are insensitive to signal amplitude changes and particularly suitable for heart rate detection. If the similarity is considerable, the weighting factor $\mu(SNR)$ is also high.

When the adjustment between a single signal episode and the averaged signal episode is optimal, it is calculated on the basis of the energy transmission how much of the output energy of the adapted filter 406 can be used as the output energy of the filter normalized with the energy of the impulse response. Thus the computational value can be obtained for the energy transmission TR as follows, for example:

$$TR = \frac{\text{square of filter output}}{\text{quadratic sum of input signal episode} \cdot \text{quadratic sum of impulse response}}$$

i.e.

$$TR = \frac{\left(\sum_{i=1}^{N} x_i \cdot h_i\right)^2}{\sum_{i=1}^{N} x_i^2 \cdot \sum_{i=1}^{N} h_i}$$

$$TR = \frac{1}{1 + \text{noise energy/signal energy}}.$$

$$SNR_{se} = \frac{\text{signal energy}}{\text{noise energy}} = \frac{TR}{1-TR}$$

The impulse response, i.e. the wave form of the signal episode, becomes more accurate as the number of signal episodes increases. The higher the SNR of the signal episodes used for averaging is, the smaller the number of signal episodes needed in averaging to achieve a certain accuracy of the impulse response, i.e. the wave form of the signal episode. Thus, according to the solution of the invention, each signal episode can be provided with a weighting value $\mu(SNR)$ dependent on the transmission or the SNR estimate. The weighting function $\mu(SNR)$ dependent on the energy transmission may be a function which depends linearly on the transmission ($\mu(SNR)=k\cdot TR$), or a function which emphasizes high transmission values progressively, either gently ($\mu(SNR)=k\cdot(TR/(1-TR))$), or more steeply ($\mu(SNR)= k\cdot(TR/(1-TR))^2$) where k is constant.

Figure 5A:
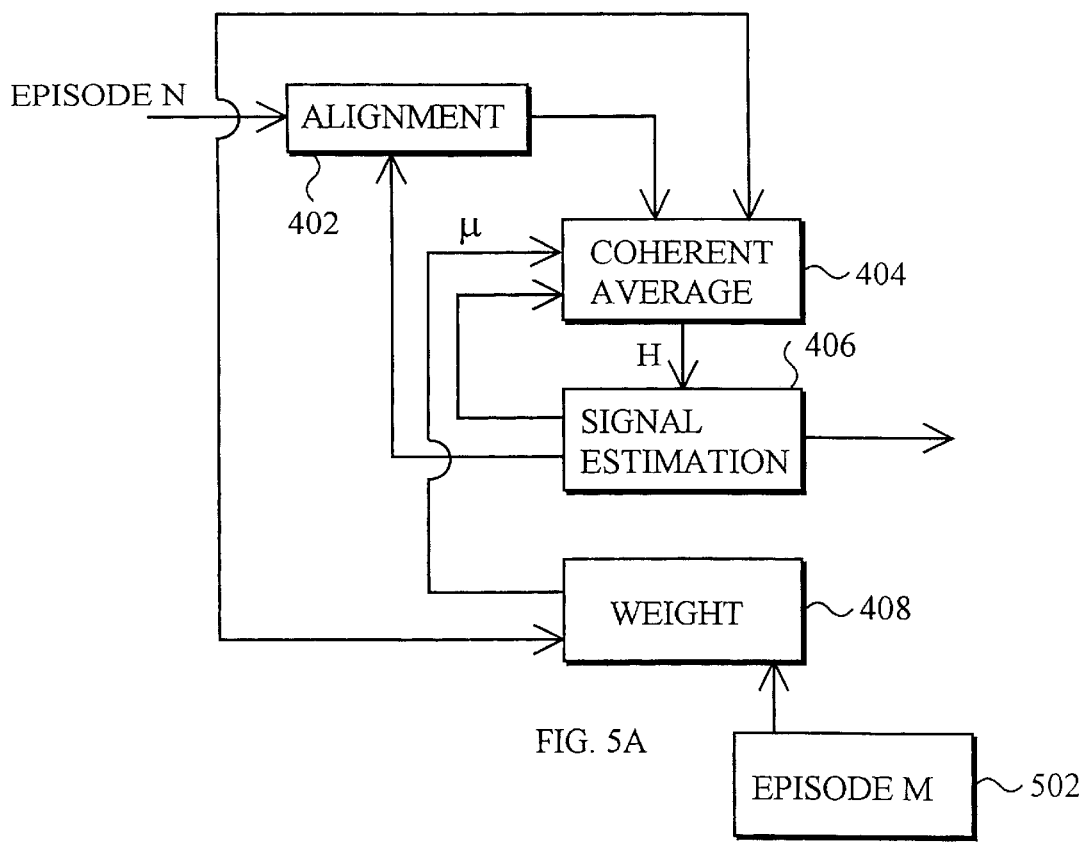
FIG. 5A illustrates a measuring arrangement employing coherent averaging and weighting.

The solution of FIG. 5A is very similar to that of FIG. 4. The average of the signal estimate to be calculated is weighted for calculation of the average. The solution comprises a signal estimate, signal adjustment block 402, coherent average calculation block 404, signal estimate determination block 406, weighting unit 408 and memory 502 in which a signal episode M preceding the present signal episode N has been stored. The weighting unit 408 determines the quality of the present signal episode N by comparing it with the earlier signal episode M. Otherwise the procedures carried out in the blocks are the same as those carried out in the case of FIG. 4.

Figure 5B:
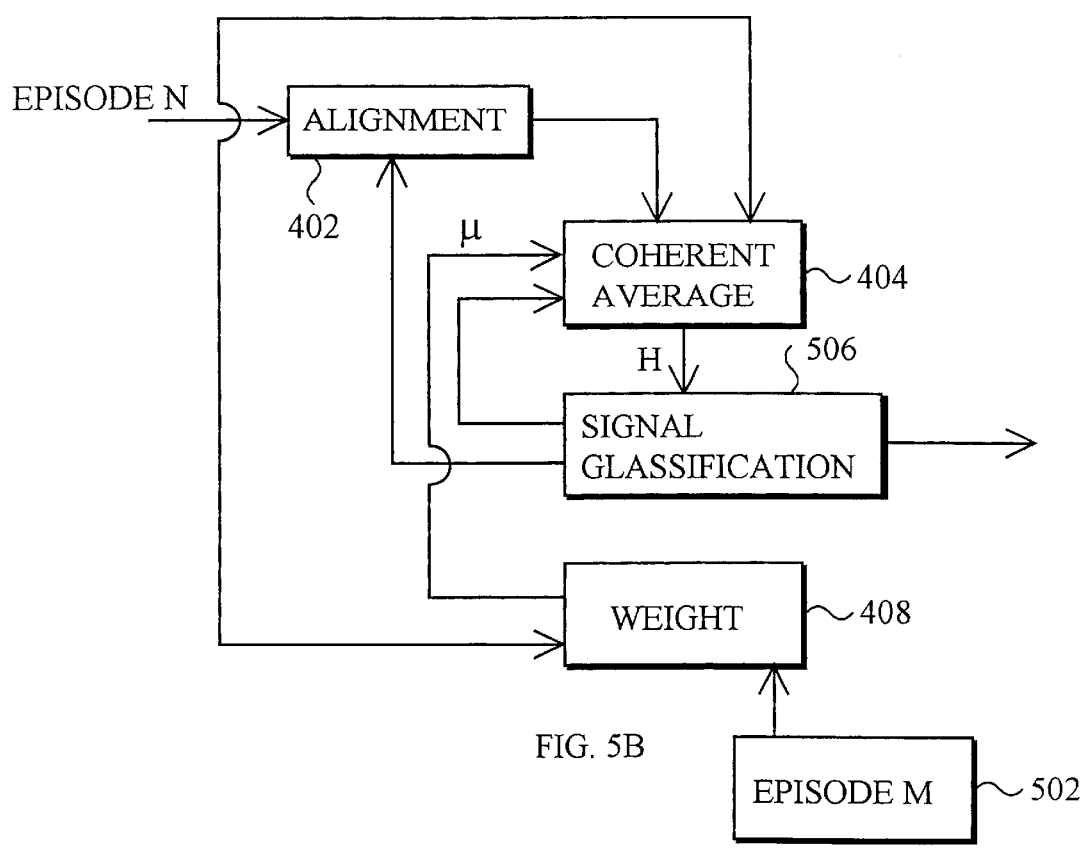
FIG. 5B illustrates classification of signals.

FIG. 5B shows a block diagram resembling the inventive solution of FIG. 5A. The solution comprises a classifier 506 which is similar to blocks 306 and 406 of FIGS. 3 and 4. This solution, however, differs from the above-mentioned ones in that, using coherent averaging of signals which is performed in block 404, signal episodes are classified into predetermined classes in block 506 by comparing a single signal episode with a signal estimate determined by means of coherent averaging. An advantage of this inventive solution is that the different signal episodes that have occurred can be recognized and analyzed after measuring. This solution is needed if, for example, the person whose heart rate is measured suffers from arrhythmia and one wants to now what kind of electric EKG changes take place during arrhythmia or what may cause arrhythmia. Such a classifier 506 forms groups of the measured wave forms of the signal episodes, and thus it can be told e.g. how many pulses of all the detected EKG pulses were in accordance with the normal QRS wave, how many pulses had changed in a certain way (e.g. widened pulse) and how many pulses had changed in some other way (e.g. inverted pulse).

Figure 6:
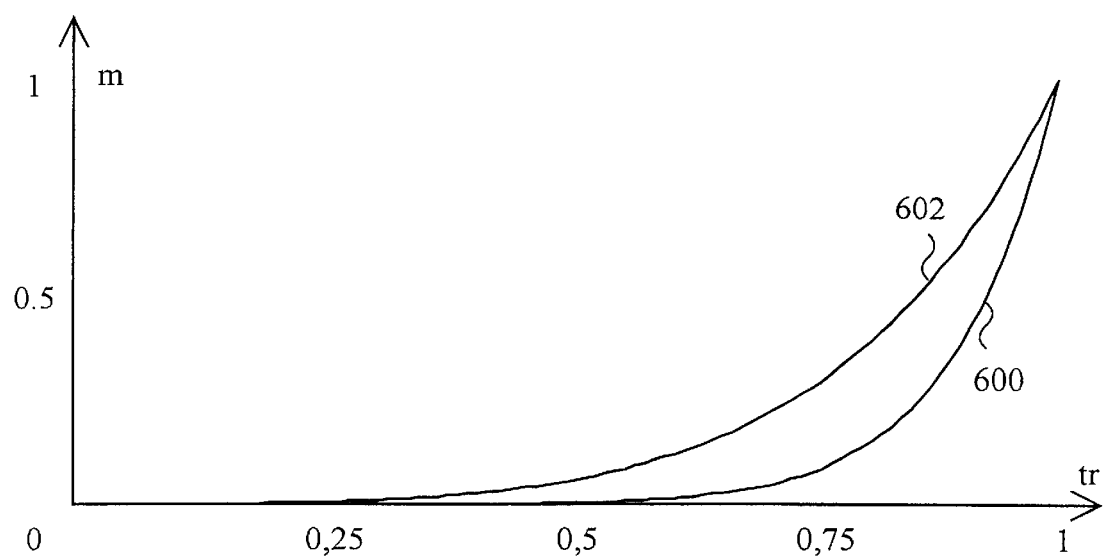
FIG. 6 illustrates two weighting functions as an example.

FIG. 6 illustrates weighting functions which change progressively according to transmission. A steep curve, such as curve 600, ensures good noise tolerance; yet it also enables slow learning if the signal episode changes. A gentle curve, such as curve 602, enables rapid learning when the signal episode changes, but if there is a lot of noise, the gentle curve may be too sensitive to noise. In both cases constant i can be used for setting the magnitude (~0.1) of the minimum step of the averaging process.

In signal detection and/or averaging a poor signal episode can be preferably eliminated using a fixed or an adaptive preset minimum value which the similarity between the signal episode and the reference signal should exceed so that the signal episode could be accepted for detection and/or averaging. As the quality of the signal episodes changes, the minimum value can be changed adaptively so that, when the quality of the signal episode becomes worse, the minimum value increases and vice versa. The minimum value may be e.g. 0.5 when the similarity of the signals is compared using normalized correlation the values of which vary within a range of [−1, ..., 1]. If the similarity of the signals exceeds the predetermined minimum value of the variable describing the signal quality, which may be e.g. 0.8 to 1, averaging can be finished. Thus the power consumption of the apparatus can be preferably reduced by switching unnecessary circuits off. In addition, weighting performed for averaging is preferably recursive in the inventive solution.

Naturally, the solution of the invention can also be applied to multi-channel signal detection. In a 2-channel measuring device, for example, each channel requires an adapted filter of its own, and the outputs of the filters of the different channels are combined into one signal with a spatial adapted filter. This is used e.g. in QRS detection based on the multi-channel EKG measurement in which the EKG signal is measured using several electrodes in different positions, and thus a QRS complex with a different wave form is obtained from each measurement point. In that case each channel is provided with an adapted filter of its own and the outputs of different channels are supplied to a common spatial adapted filter. The solution of the invention is also applicable to detection of the pressure pulse of an artery. In that case the solution comprises several channels each of which has an adapted filter and which are selected and weighted by means of a spatial adapted filter. In addition, the solution of the invention can be also used to warn of poor contact between the electrode and the skin, to select noise-free sections of the EKG signal and to prevent analysis and update of signal episodes when the signals contain noise.

Even though the invention has been described above with reference to the example illustrated in the accompanying drawings, it will be obvious that the invention is not limited to it, but may be modified in several ways within the scope of the inventive concept disclosed in the appended claims.

What is claimed is:

1. A method of measuring a recurrent signal episode of a vital function, the method employing an adapted filter for detecting the signal episode, the method comprising
    weighting a single signal episode with a weighting value ($\mu$) which depends on the quality of the single signal episode, and
    calculating a coherent average of single signal episodes to determine the wave form of the signal episode.

2. A method according to claim 1, wherein the signal episode is the QRS complex of the heart rate.

3. A method according to claim 1, wherein weighting is recursive.

4. A method according to claim 1, wherein the magnitude of the weighting value is a function of the signal-to-noise ratio or the like describing the quality of a single signal episode.

5. A method according to claim 4, wherein to determine the weighting value ($\mu$), the quality of a single signal episode is determined by means of a sample correlation coefficient or energy transmission of the adapted filter.

6. A method according to claim 1, wherein to determine the weighting value ($\mu$), the quality of a single signal episode is determined by comparing the single signal episode with the signal estimate calculated using coherent averaging.

7. A method according to claim 6, wherein averaging is finished when the similarity obtained as a result of the comparison is greater than the predetermined minimum value of the variable describing the signal quality.

8. A method according to claim 1, wherein to determine the weighting value ($\mu$), the quality of a single signal episode is determined by comparing the single signal episode with another single signal episode.

9. A method according to claim 1, wherein the signal episode is taken into account in calculation of the coherent average if the energy transmission of the signal episode in the adapted filter exceeds a preset minimum value.

10. A method according to claim 9, wherein the preset minimum value is adjusted adaptively according to the quality of the signal episode.

11. A method according to claim 9, wherein the poorer the quality of the signal episode, the higher the threshold value.

12. A method according to claim 1, wherein single signal episodes are classified into predetermined classes by comparing a single signal episode with a signal estimate determined by means of coherent averaging.

13. A method of determining the impulse response (H) of a recurrent signal episode of a vital function in a detector based on an adapted filter, the method comprising
    calculating a coherent average of single signal episodes, the signal episodes being weighted for averaging with a weighting value ($\mu$) that depends on the quality of the single signal episodes, and
    employing the coherent average of the signal episode for forming the impulse response of the adapted filter.

14. A method according to claim 13, wherein the signal episode is the QRS complex.

15. A method according to claim 13, wherein a single signal episode is weighted for averaging with a weighting value ($\mu$) which depends on the quality of the single signal episode, and a coherent average of the weighted signal episodes is calculated.

16. A method according to claim 13, wherein weighting is recursive.

17. A method according to claim 13, wherein the signal episode is taken into account in calculation of the coherent average if the energy transmission of the signal episode in the adapted filter exceeds a preset minimum value.

18. A measuring device for measuring a recurrent signal episode for a vital function, the measuring device comprising electrodes for receiving signal episodes generated by the vital function and an adapted filter for detecting the signal episodes received by the electrodes, the measuring device further comprising
    a weighting unit which is arranged to weight a single signal episode with a weighting value which depends on the quality of the single signal episode; and
    a coherent averaging unit for determining the wave form of the signal episode received by the electrodes.

19. A measuring device according to claim 15, wherein the signal episode is the QRS complex of the heart rate.

20. A measuring device according to claim 19, wherein the weighting unit is arranged determine the weighting value ($\mu$) as the function of the signal-to-noise ratio or the like describing the quality of a single signal episode.

21. A measuring device according to claim 20, wherein the averaging unit does not perform averaging if the similarity obtained as a result of the comparison is greater than the predetermined threshold value.

22. A measuring device according to claim 19, wherein the weighting unit is arranged to determine the quality of a single signal episode by comparing the single signal episode with the signal episode determined in the coherent averaging unit.

23. A measuring device according to claim 19, wherein
the weighting unit is arranged to determine the quality of a single signal episode by comparing the single signal episode with another signal episode.

24. A measuring device according to claim 22, wherein the averaging unit does not perform averaging if the similarity obtained as a result of the comparison is greater than the predetermined threshold value.

25. A measuring device according to claim 18, wherein
the weighting unit is arranged to determine the quality of a single signal episode by means of a sample correlation coefficient or energy transmission of the adapted filter.

26. A measuring device according to claim 25, wherein the measuring device is arranged to adjust the threshold value of energy transmission adaptively according to the quality of the signal episode.

27. A method according to claim 8, wherein averaging is finished when the similarity obtained as a result of the comparison is greater than the predetermined minimum value of the variable describing the signal quality.

28. A measuring device for measuring a recurrent signal episode of a vital function, the measuring device comprising electrodes for receiving signal episodes generated by the vital function, the measuring device further comprising:

a weighting unit arranged to weight a single signal episode with a weighting value which depends on the quality of the single signal episode;

a coherent averaging unit for calculating a coherent average of the signal episodes received by the electrodes, and an adapted filter having an impulse response based on the coherent average of the signal episode.

29. A measuring device according to claim 28, wherein the adapted filter is arranged to determine energy transmission and the measuring device is arranged to take the signal episode into account if the energy transmission of the signal episode exceeds the threshold value.

30. A measuring device according to claim 29, wherein the poorer the quality of the signal episode, the higher the threshold value.

31. A measuring device according to claim 28, wherein the measuring device comprises a classifier which is arranged to classify single signal episodes into predetermined classes by comparing the single signal episode with the signal estimate determined by coherent averaging.

32. A measuring device according to claim 28, wherein the signal episode is the QRS complex.

33. A measuring device according to claim 28, wherein the measuring device comprises a weighting unit which is arranged to weight a single signal episode with a weighting value which depends on the quality of the single signal episode.

34. A method of determining the impulse response (H) of a recurrent signal episode of a vital function in a detector based on an adapted filter, the method comprising weighting a single signal episode with a weighting value ($\mu$) which depends on the quality of the single signal episode;

calculating a coherent average of single signal episodes; and employing the coherent average of the signal episode for forming the impulse response of the adapted filter.

35. A measuring device for measuring a recurrent signal episode of a vital function, the measuring device comprising electrodes for receiving signal episodes generated by the vital function, the measuring device further comprising a weighting unit which is arranged to weight a single signal episode with a weighting value which depends on the quality of the single signal episode, a coherent averaging unit for calculating a coherent average of the signal episodes received by the electrodes; and an adapted filter having an impulse response based on the coherent average of the signal episode.

* * * * *

UNITED STATES PATENT AND TRADEMARK OFFICE
CERTIFICATE OF CORRECTION

PATENT NO. : 6,282,439 B1
DATED : August 28, 2001
INVENTOR(S) : Ruha

It is certified that error appears in the above-identified patent and that said Letters Patent is hereby corrected as shown below:

Title page,
*Attorney, Agent,* or *Firm,* now reads "Hoffman & Baron, LLP"; this should read
-- Hoffmann & Baron, LLP --.

Column 6,
Line 5, please insert the following:

-- where $x_i = s_i + n_i$ (each signal sample consists of a signal $s_i$ component and a noise $n_i$ component). The expression of energy transmission can be reduced as follows $$TR = \frac{1}{1 + noise\ energy/signal\ energy},$$

i.e. the transmission represents a momentary signal-to-noise ratio SNR. On the basis of the transmission the following dependency, for example, can be obtained for the signal-to-noise ratio SNR of the signal episode energy: --
Line 60, now reads "i can be used for setting ..."; this should read -- μ can be used for setting ... --

Signed and Sealed this

Sixth Day of August, 2002

*Attest:*

*Attesting Officer*

JAMES E. ROGAN
*Director of the United States Patent and Trademark Office*